(12) United States Patent
Goto et al.

(10) Patent No.: US 6,563,115 B1
(45) Date of Patent: May 13, 2003

(54) HIGH-DENSITY RECORDING SCANNING MICROSCOPE

(75) Inventors: Katsuto Goto, Shinjuku-ku (JP); Takashi Shimaya, Shinjuku-ku (JP); Yutaka Hirano, Shinjuku-ku (JP); Hiroyuki Teshima, Shinjuku-ku (JP)

(73) Assignee: Sanyu Denshi Co. Ltd., Tokyo (JP)

( * ) Notice: Subject to any disclaimer, the term of this patent is extended or adjusted under 35 U.S.C. 154(b) by 0 days.

(21) Appl. No.: 09/673,170
(22) PCT Filed: Feb. 21, 2000
(86) PCT No.: PCT/JP00/00957
§ 371 (c)(1), (2), (4) Date: Dec. 18, 2000

(30) Foreign Application Priority Data

Feb. 24, 1999 (JP) .......................................... 11-046929
Mar. 5, 1999 (JP) .......................................... 11-059474

(51) Int. Cl.⁷ .......................... G01N 23/00; G21K 7/00
(52) U.S. Cl. ................................................ 250/311
(58) Field of Search ................................. 250/306, 310, 250/311, 492

(56) References Cited

U.S. PATENT DOCUMENTS

| | | | | |
|---|---|---|---|---|
| 5,051,585 A | * | 9/1991 | Koshishiba et al. | 250/310 |
| 6,047,083 A | * | 4/2000 | Mizuno | 382/141 |
| 6,067,153 A | * | 5/2000 | Mizuno | 356/237.2 |
| 6,348,690 B1 | * | 2/2002 | Iwabuchi et al. | 250/310 |
| 6,426,501 B1 | * | 7/2002 | Nakagawa | 250/310 |
| 6,452,178 B2 | * | 9/2002 | Iwabuchi et al. | 250/310 |
| 6,476,400 B1 | * | 11/2002 | Robinson et al. | 250/492.22 |

* cited by examiner

Primary Examiner—Jack Berman
Assistant Examiner—Johnnie L Smith, II
(74) Attorney, Agent, or Firm—Staas & Halsey LLP (57) ABSTRACT

A high-density recording scanning microscope in which a beam of charged particles finely focused scans the surface of a sample at a high density of, at least, 8,000 scannings, a signal thus detected is converted into a digital signal, and the digital signal is used for directly printing an image of high definition, high gradation and wide view. The signal of a scanning image at a very high density of, at least, 8,000 pixels×8,000 pixels in a scanning electron microscope, is converted into a digital signal, for example, a color image, and the image is directly printed, thereby to realize the observation of a very clear image of high definition, high gradation and wide view having hitherto been nonexistent.

7 Claims, 6 Drawing Sheets

FIG. 2A  CONVENTIONAL SCREEN

FIG. 2B

SCREEN (VIRTUAL SCREEN) IN PRESENT INVENTION

EXAMPLE OF ADJUSTING SCREEN
(SEM. CONTRAST/BRIGHTNESS)

FIG. 4B

○ MEMORY STORES 16,000 x 16,000 PIXELS
○ PIXEL DATA: 12 BITS

FIG. 4C

○ NUMBER OF PIXELS ARE 16,000 x 16,000
○ PIXEL DATA: 8 BITS FOR EACH OF R, G AND B (12-BIT DATA IS CONVERTED INTO 8-BIT DATA BY COLORING)

FIG. 5A

○ 16,000 x 16,000
○ COLOR IMAGE

FIG. 5B

| FILE ① | 16,000 x 4,096 |
| FILE ② | 16,000 x 4,096 |
| FILE ③ | 16,000 x 4,096 |
| FILE ④ | 16,000 x 4,096 |

(FILE FORMAT IS BMP OR TiF)

FIG. 5C

SAVED DATA

FILE ①
⸱
FILE ④

SENDING FILES IN SUCCESSION

PRINTING IMAGE OF 16,000 x 16,000 PIXELS

FIG. 6

| | R | G | B |
|---|---|---|---|
| (0) | 255 | 255 | 255 |
| (1) | 254 | 255 | 255 |
| 2 | 255 | 254 | 255 |
| 3 | 255 | 255 | 254 |
| 4 | 253 | 255 | 255 |
| 5 | 255 | 253 | 255 |
| 6 | 255 | 255 | 253 |
| 7 | 252 | 255 | 255 |
| 8 | 255 | 252 | 255 |
| 9 | 255 | 255 | 252 |
| 10 | 251 | 255 | 255 |
| 11 | 255 | 251 | 255 |
| 12 | 255 | 255 | 251 |
| 13 | 250 | 255 | 255 |
| 14 | 255 | 250 | 255 |
| 15 | 255 | 255 | 250 |
| 16 | 254 | 254 | 254 |
| 17 | 253 | 254 | 254 |
| ... | | | |
| 4092 | 0 | 2 | 0 |
| 4093 | 0 | 0 | 2 |
| 4094 | 0 | 1 | 1 |
| 4095 | 0 | 0 | 0 |

R, G AND B OF PIXEL (8 BITS FOR EACH COLOR)

PIXEL VALUE (GRADATION LEVEL) OF 12 BITS

HIGH-DENSITY RECORDING SCANNING MICROSCOPE

BACKGROUND OF THE INVENTION

1. Field of the Invention

The present invention relates to a high-density recording scanning microscope in which a beam of charged particles is finely focused to scan the surface of a sample at a high density of, at least, 8,000 scannings, and a detected signal is converted into a digital signal, so as to directly print an image of high definition, high or rich gradation and wide view. More particularly, it relates to techniques with which a very clear image of high definition, high gradation and wide view having, for example, at least 8,000 pixels×8,000 pixels and having hitherto been nonexistent, is directly printed in, for example, colors.

2. Description of the Related Art

With a scanning electron microscope, an enlarged scanning image has heretofore been observed in such a way that a sample is submitted to planar scanning while being irradiated with an electron beam which is a finely focused beam of charged particles, so as to detect secondary electrons or the likes generated on this occasion, and that the enlarged scanning image is displayed on a cathode-ray tube through brilliance modulation, that the image on the cathode-ray tube is photographed with a Polaroid film (registered trademark) or that it is photographed with a conventional film and is printed on sensitized paper.

Besides, the photographing has been done in such a way that, at a high magnifying power, focusing and astigmatism compensation are performed into a state where the image on the cathode-ray tube is substantially focused, whereupon the magnifying power is lowered.

On account of its property, the scanning electron microscope in the prior art needs to detect the secondary electrons or the likes generated when the surface of the sample is scanned using an electron-beam spot, and to display the image through the brilliance modulation of the cathode-ray tube with the detected signal. For the observation or photographing, therefore, the displaying cathode-ray tube or even the photographing cathode-ray tube of high resolution can display only a rectangular image whose resolution is about 500 through 1,600 pixels, or about 2,500 pixels at the utmost. As a result, the prior-art scanning electron microscope has such a narrow view that only the image of a very small area, for example, an area of 0.02 mm×0.02 mm when the sample is scanned at scanning intervals of 0.01 $\mu$m at a density of 2,000 pixels×2,000 pixels, can be recorded by one time of photographing and then observed. This has posed the problem that the troublesome job of repeatedly photographing adjacent areas so as to overlap each other, and creating an image of wide view by pasting the images of the individual areas, is required.

On the other hand, when a large area is entirely photographed, a low-density image is obtained because the number of scanning lines is as small as, for example, about 2,000×2,000 at the utmost. This has posed the problem that, even when part of the photographed image is taken out and enlarged, the image of the fine part cannot be observed.

Further, the photographing cathode-ray tube of high resolution creates an image by exposing a film to a minute light spot luminescing when a phosphor screen coated with a fluorescent material is scanned with an electron beam. This has posed the problem that the image is usually a monochromatic one, the gradation of which is too narrow to expose the film to a large number of gradation levels, for example, gradation levels of 12 bits and to print the gradation levels on sensitized paper.

SUMMARY OF THE INVENTION

In order to solve the problems stated above, the present invention has its object to provide a high-density recording scanning microscope in which a beam of charged particles finely focused scans the surface of a sample at a high density of, at least, 8,000 scannings, a signal thus detected is converted into a digital signal, and the digital signal is used for directly printing an image of high definition, high gradation and wide view, particularly a very clear image of high definition, high gradation and wide view having at least 8,000 pixels×8,000 pixels and having hitherto been nonexistent.

According to the present invention, the surface of a sample is scanned with a spot of charged particles focused by an objective lens, at a high density of, at least, 8,000 scannings for printing, and it is scanned in a direction substantially orthogonal to the direction of the first-mentioned scanning, at the high density of, at least, 8,000 scannings, or the sample surface is scanned with the number of scannings at a low density for displaying, the number of scannings being smaller than in the high-density printing, and it is scanned in a direction substantially orthogonal to the direction of the low-density scanning, with the number of scannings at the low density, a signal generated or absorbed by the scanning is detected, the signal detected at the high density is converted into a digital signal, and printing is done on the basis of the converted digital signal, or the displaying is done on the basis of the signal detected at the low density.

Herein, during the high-density scanning, the size of the spot is made substantially equal to or somewhat smaller than a scanning interval at the high density by the objective lens or a dynamic focusing coil separately disposed.

Besides, the converted digital signal is stored in a memory, and the printing is done on the basis of the digital signal read out of the memory.

In addition, the detected signal is converted into a digital color signal.

Further, a table in which color gradation levels corresponding to the gradation levels of the detected signal are registered is comprised, and the detected signal is converted into a color signal by reference to the table.

Still further, in converting the detected signal into a color signal, the detected signal is converted into the gradation level of the color signal corresponding to that of the detected signal, on the basis of two designated colors.

Yet further, the detected signal is set at, at least, 8 bits, and when the color signal consists of R, G and B signals, each of them is composed of 8 bits, or when the color signal is for the printing, the color signal has colors in a color data format for use in the printer, and the number of bits of the colors.

PREFERRED EMBODIMENTS OF THE INVENTION

Figure 1:
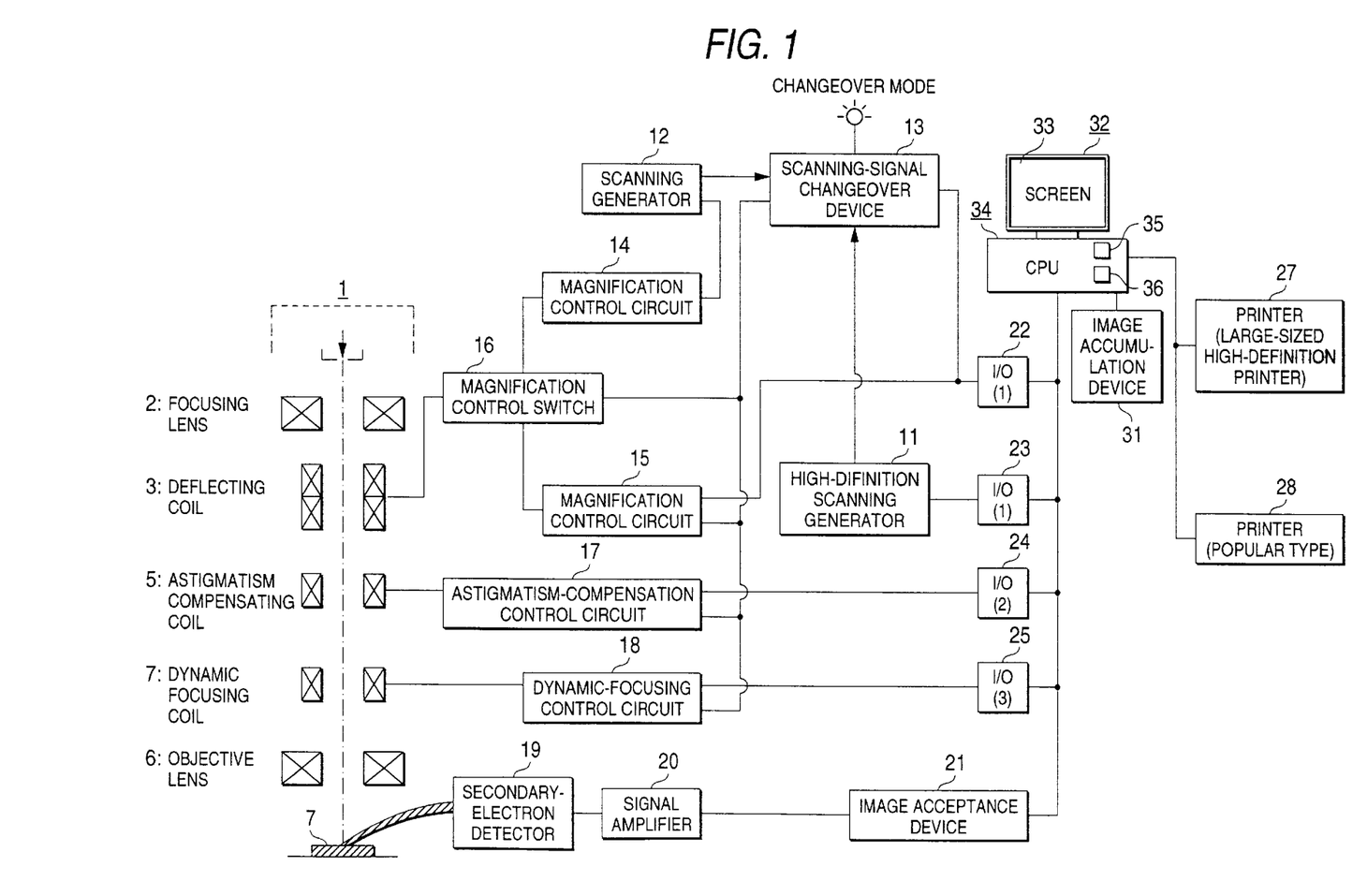
FIG. 1 is a block diagram showing a system architecture according to the present invention.

FIG. 1 shows a block diagram of a system architecture according to the present invention.

Referring to the figure, an irradiation system 1 functions to generate and focus an electron beam being a beam of charged particles, and to submit the surface of a sample 7 to planar scanning in a state where the sample 7 is irradiated with the finely focused beam. The irradiation system 1 is constructed having constituents 2 through 6. The charged particles include, not only electrons having negative charges, but also the particles of ions (such as primary ions or secondary ions) etc. having positive charges. The present invention is applicable to these charged particles similarly. Here, for the brevity of description, the electrons shall be taken as an example.

The focusing lens 2 focuses the electron beam produced from an electron gun, not shown, and then accelerated.

The deflecting coil 3 deflects an electron-beam spot focused finely and projected on the sample 7, so as to implement the planar scanning (planar scanning in which linear scanning in a certain direction and linear scanning in a direction substantially orthogonal to the certain direction are performed at predetermined line intervals).

The astigmatism compensating coil 4 compensates the astigmatism of the electron-beam spot so as to focus this spot into a circular shape.

The dynamic focusing coil 5 dynamically focuses the electron-beam spot into a fine one even when this electron-beam spot irradiates that position on the sample 7 which deviates from a central view position. Here, in a case where the interval of scanning lines has been changed by changing a magnifying power or the number of scanning lines and where the adjacent scanning lines have left an unscanned space therebetween or have overlapped each other at the linear scanning with the electron-beam spot, the dynamic focusing coil 5 may well be operated in interlocking by feeding a current so as to endow the electron-beam spot with a size which is substantially equal to or somewhat smaller than the scanning line interval.

The objective lens 6 focuses the electron-beam spot finely and projects this spot on the sample 7. Since high-density scanning of 8,000 scanning lines or more is performed here, the size of the electron-beam spot should desirably be made substantially equal to or somewhat smaller than the scanning line interval which is determined by the number of scanning lines and the magnifying power, and a current to be fed to the objective lens 6 is controlled for that purpose. The control is performed, for example, in such a way that the values of the currents to be fed to the objective lens 6 and the dynamic focusing coil 5 (the current values of differences from just focusing where the electron-beam spot is focused to the minimum size) are experimentally found beforehand in correspondence with the scanning line intervals determined by the number of scanning lines and the magnifying power, that the current values found are set in a table, and that the predetermined currents are fed to the objective lens 6 and the dynamic focusing coil 5 by referring to the table. On this occasion, the dynamic focusing coil 5 and the objective lens 6 are interlockingly controlled so as to control a defocus of small magnitude by the former 5 and to control a defocus of large magnitude by the latter 6. Besides, in a case where the magnifying power is especially as low as several hundred magnifications~ten odd magnifications, a good image is obtained even with the electron-beam spot which is smaller as compared with the scanning line interval. In the case of the low power, however, a sample area corresponding to about 10% of the scanning line interval is scanned by the electron-beam spot when the sample 7 is scanned by, at least, 8,000 scannings in the state where the size of the electron-beam spot is smaller as compared with the scanning line interval, for example, in a state where the magnifying power is one hundred magnifications and where the electron-beam spot is focused to the minimum size of about 50 angstroms. Consequently, a signal is detected only from the area scanned by the small-sized electron-beam spot, and an image is printed. In observing the printed image, accordingly, it needs to be considered that information could not be detected from the remaining area which had not been scanned by the electron-beam spot.

The sample 7 is a subject for detecting a signal generated or absorbed on the occasion of the planar scanning with the electron-beam spot, and for displaying or printing a high-definition image.

A high-definition scanning generator 11 included in the system architecture generates scanning signals (scanning signals in a horizontal direction and a vertical direction) of high precision (for example, 16,000 pixels×16,000 pixels in an experiment where the number of pixels is larger than 8,000 pixels×8,000 pixels) for generating an image signal of high definition. When images were actually printed, the effects of a clear reproduction, a high definition, a wide view and a high or rich gradation were recognized at and above 8,000 pixels×8,000 pixels. In the experiment, a scanning generator of high stability especially designed for 16,000 scannings×16,000 scannings was employed so that an image of more effective 16,000 pixels×16,000 pixels could be printed.

A scanning generator 12 generates scanning signals of low precision (for example, 500 pixels×500 pixels) for use in a conventional scanning electron microscope or the like.

A scanning-signal changeover device 13 changes-over the scanning signals of high precision and those of low precision at will in correspondence with a changeover mode instructed externally.

A magnification control circuit 14 delivers the signal of designated magnifications on the basis of the low-precision scanning signals fed from the scanning generator 12.

A magnification control circuit 15 delivers the signal of designated magnifications on the basis of the scanning signals fed from the scanning-signal changeover device 13.

A magnification control switch 16 changes-over the signals of the magnification control circuits 14, 15 and the scanning-signal changeover device 13 and selects any of them, and it feeds the selected signal to the deflecting coil 3, whereby a scanning current or the like for establishing predetermined magnifications is fed to the deflecting coil 3.

An astigmatism-compensation control circuit 17 feeds the current to the astigmatism compensating coil 4, thereby to compensate the astigmatism of the electron-beam spot.

A dynamic-focusing control circuit 18 feeds the current to the dynamic focusing coil 5, thereby to dynamically focus the electron-beam spot (as the electron-beam spot is deflected to deviate from the view center on the sample 7, it becomes defocused, and hence, the current is fed in synchronism with the scanning signals so as to keep the electron-beam spot focused, thereby to compensate the defocus).

A secondary-electron detector 19 detects secondary electrons emitted when the surface of the sample 7 is submitted to the planar scanning with the electron-beam spot.

A signal amplifier 20 amplifies a signal (image signal) detected by the secondary-electron detector 19.

An image load device 21 converts into a digital image signal the analog signal (image signal) which indicates the intensity of the secondary electrons or the likes emitted from the sample 7 and which has been amplified by the signal amplifier 20 (for example, the digital image signal is obtained in such a way that the whole scanning range of the surface of the sample 7 is sampled in synchronism with the horizontal scanning signal and the vertical scanning signal so as to become 16,000×16,000 pixels larger in number than 8,000×8,000 pixels, and that the sampled pixels are quantized into data of 12 bits).

I/O 22 through 25 are input/output circuits which transfer signals between a CPU 34 and the magnification control circuit 15, the high-definition scanning generator 11, the astigmatism-compensation control circuit 17 and the dynamic-focusing control circuit 18, respectively. By way of example, each of the I/O 22 through 25 is used for signal controls such as D/A conversion in which a digital signal from the CPU 34 is converted into an analog signal.

A printer (large-sized high-definition printer) 27 is a color printer (such as plotter or ink jet printer) of large size (for example, A0 format) and high definition.

A printer (of popular type) 28 is a color printer having an ordinary size (for example, A3 format).

An image accumulation device 31 is a memory in which digital image signals of high definition (of, for example, 16,000×16,000 pixels) are accumulated.

A display device 32 displays an image of low resolution (500 through 1,800 pixels), and it may be any of a color CRT, a color liquid-crystal display, a general household television receiver, etc.

A screen 33 is of the display device 32, and an image is displayed thereon.

The CPU 34 executes various processes in accordance with programs. Here, it is constructed having image editing means 35 and image conversion means 36 which are operated by the programs.

The image editing means 35 edits an image so as to display the image on the screen 33.

The image conversion means 36 operates, for example, to convert a monochromatic image signal into a color image signal (to convert a monochromatic image signal into a color image signal without degrading the gradation of the former).

Here will be described the steps of procedure in the case where an image of high definition, wide view and high gradation is printed under the architecture of FIG. 1:

(1) In a state where an electron beam produced in the irradiation system 1 is focused by the focusing lens 2 and is further focused by the objective lens 6, thereby to be projected on the sample 7, a low-density scanning current is fed to the deflecting coil 3. Thus, an electron-beam spot irradiated on the sample 7 is deflected to scan the surface of this sample in an X-direction and a Y-direction.

(2) Secondary electrons, which are emitted from the sample 7 while this sample 7 is being scanned with the electron-beam spot in the state of the step (1), are detected by the secondary-electron detector 19 so as to display an image on the screen 33 of the display device 32.

(3) In the state of the step (2) where the image of the area of the sample 7 scanned with the electron-beam spot is displayed on the screen 33, a direct current of high stability to be fed to the objective lens 6 is finely adjusted for focusing the electron-beam spot, and a current to be fed to the astigmatism compensating coil 4 is finely adjusted for compensating the astigmatism of the electron-beam spot, in order that the image may be displayed clearly. Here, the focusing and the astigmatism compensation are performed at a magnifying power higher than that of actual high-definition printing, and they are thereafter performed precisely by lowering the magnifying power. Besides, the brightness and contrast of the image to be displayed on the screen 33 are adjusted to the optima (refer to FIG. 4(a) and description in this specification).

(4) A position and magnifications on the sample 7 are adjusted in order that the area for the high-definition printing may be displayed.

Owing to the above steps, the adjustments of the magnifications, position, focusing, astigmatism compensation, brightness, contrast, etc. of the enlarged image of the sample 7 for the high-definition printing have been made on the screen 33 of the display device 32 by the low-density scanning.

(5) Subsequently, the mode of operation is changed-over so as to feed a high-density scanning current to the deflecting coil 3.

Figure 4A:
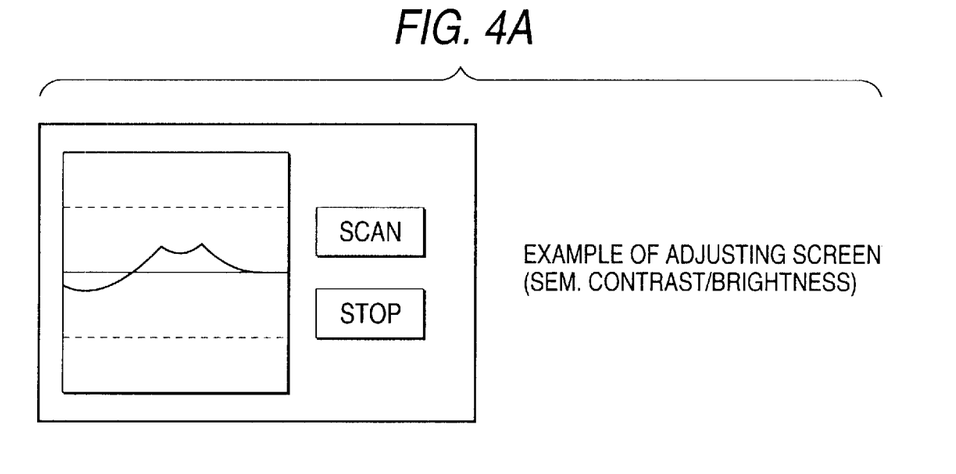
FIGS. 4(a), 4(b) and 4(c) are diagrams for elucidating data conversion (#1) in the present invention.
Figure 4B:
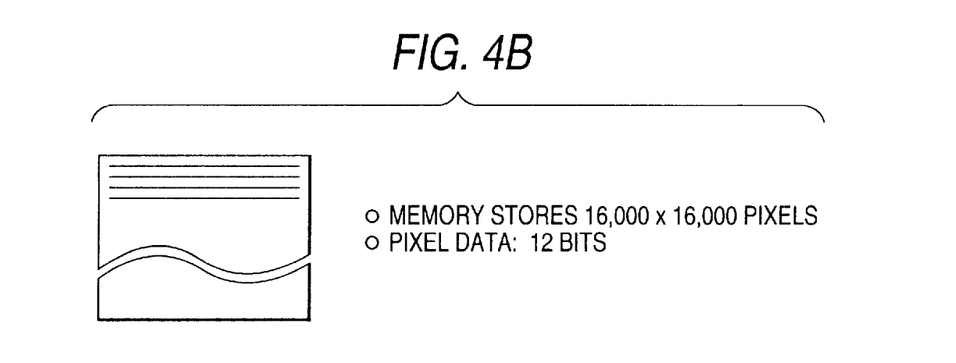

(6) The surface of the sample 7 is submitted to high-density scanning by, at least, 8,000×8,000 scannings, and a signal generated at this time is converted into a digital signal, which is stored in the image accumulation device 31 (refer to FIG. 4(b) and the explanation thereof). Simultaneously, the digital signal read out of the image accumulation device 31 is converted into a color signal, which is used for the high-definition color printing by the printer 27 (refer to FIG. 4(c) and the explanation thereof).

It is permitted by the above procedure to directly print the enlarged microscopic color image having the high definition of, at least, 8,000×8,000 pixels, the wide view and the high gradation. The operation will be described in detail below.

Figure 2A:
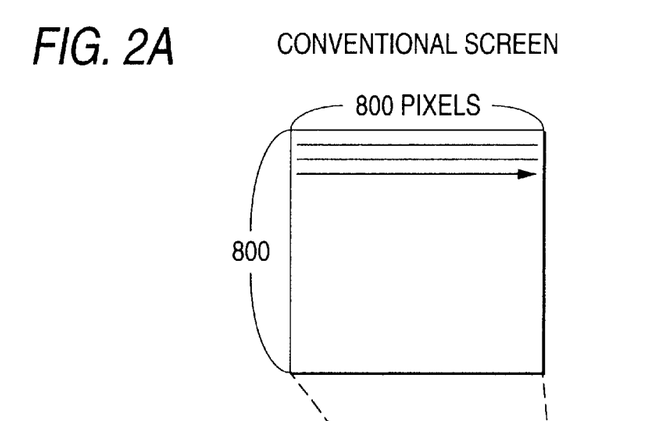
FIGS. 2(a) and 2(b) are diagrams for elucidating the adjustments of astigmatism compensation and focusing in the present invention.
Figure 2B:
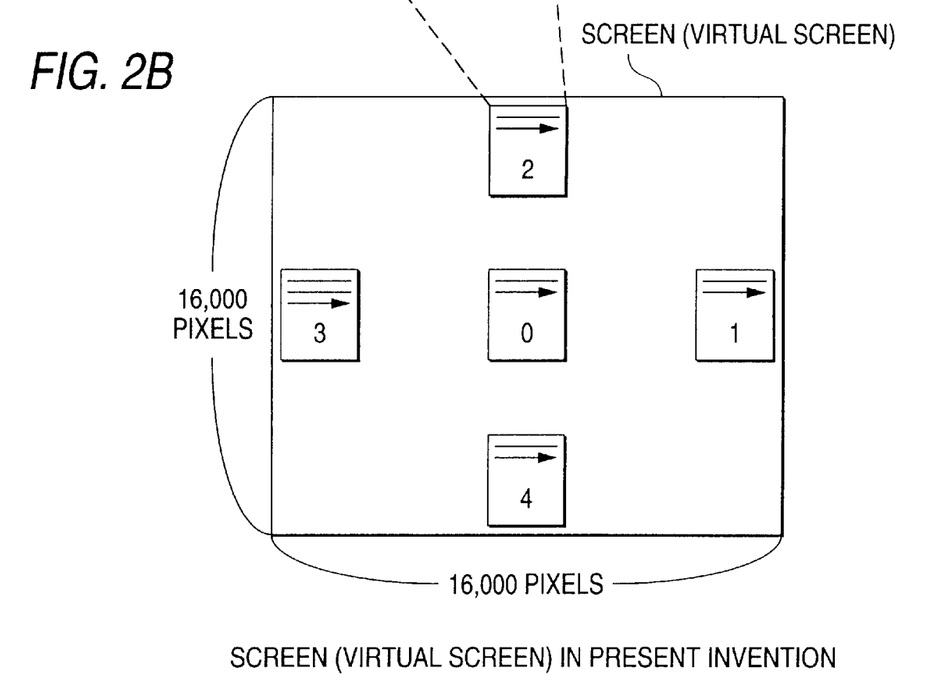

FIGS. 2(a) and 2(b) show diagrams for elucidating the adjustments of astigmatism compensation and focusing in the present invention.

FIG. 2(a) exemplifies a conventional screen. Here, the conventional screen has 800×800 pixels by way of example.

FIG. 2(b) exemplifies a screen (virtual screen) in the present invention. The virtual screen in the present invention has, for example, 16,000×16,000 pixels as indicated in the figure. As compared with the size of the conventional screen in FIG. 2(a), that of the virtual screen is 20 times larger in a lateral direction and 20 times larger in a vertical direction, and it is 20×20=400 times larger in terms of the number of pixels. With the virtual screen of the present invention, therefore, an image signal of high definition is derived as stated below. Scanning signals are controlled so as to obtain respective screens of 800×800 pixels at five positions indicated in FIG. 2(b):

00 (central position),
01 (right middle position),
02 (upper middle position),
03 (left middle position), and
04 (lower middle position), whereby the screens are successively displayed on the screen 33 of the display device 32. Alternatively, scanning signals are controlled so as to obtain a still smaller number of pixels at each of the positions 0 through 4, whereby five screens are simultaneously displayed on the five divisional parts of the screen 33 of the display device 32. Herein, focusing (dynamic focusing) and astigmatism compensation are performed on each of the five screens at the positions 0 through 4 (consequently, on an enlarged image), or focusing and astigmatism compensation are performed on the entire virtual screen automatically or manually.

Figure 3A:
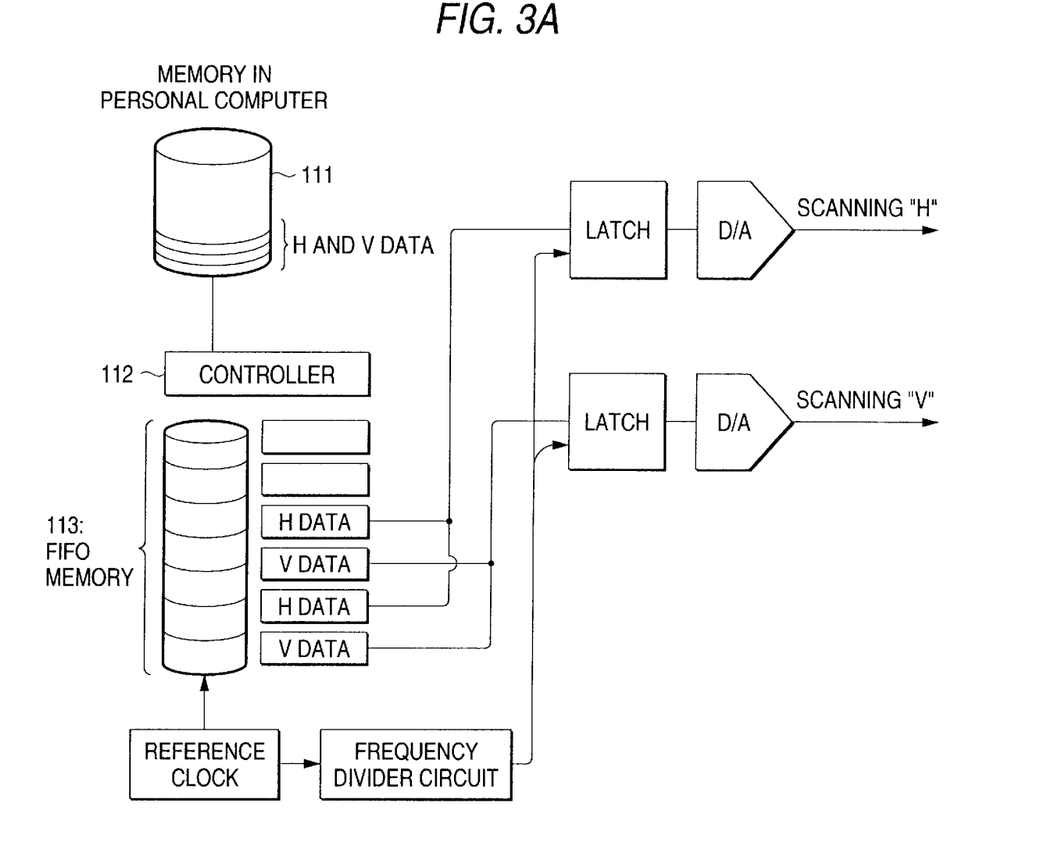
FIGS. 3(a) and 3(b) are diagrams for elucidating digital scanning in the present invention.
Figure 3B:
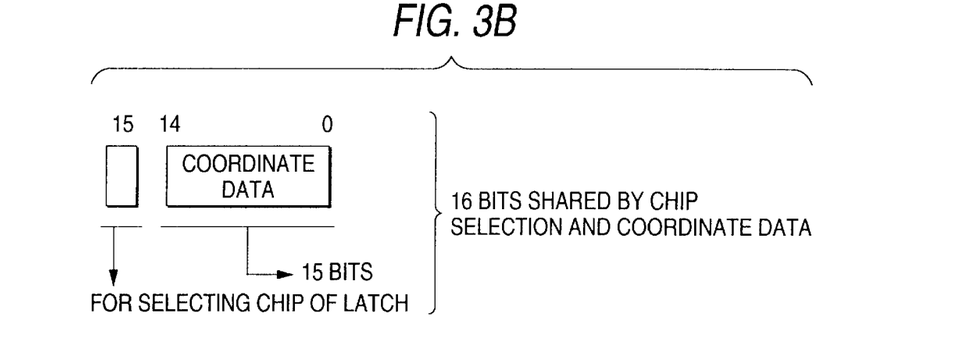

FIGS. 3(a) and 3(b) show diagrams for elucidating digital scanning in the present invention.

FIG. 3(a) shows a block diagram of the digital scanning.

Referring to FIG. 3(a), a controller 112 loads data from a memory included in a personal computer, or the like, and it stores the data in a FIFO memory 113. Further, H data and V data read out of the FIFO memory 113 in synchronism with a reference clock are respectively set in latches, and the data set in the latches are respectively converted by D/A converters into analog scanning signals (H, V), which are delivered as outputs.

As described above, the H data and V data loaded from the memory 111 and stored in the FIFO memory 113 are read out and are set in the latches, and the data set in the latches are converted into the analog scanning signals (H, V) by the D/A converters. Thus, it is permitted to scan at any desired number of steps.

FIG. 3(b) shows an example of a data format in the V and H data. Here, each of the H data and the V data is expressed by 2 bytes. The 15th bit of the 2 bytes is used for selecting the chip of the latch, and coordinate data is expressed by the remaining 15 bits.

Owing to the above construction, the chip of the latch is selected, that is, the H and V data are directly changed-over by each of the 15 bit of the data, and the coordinate data (bits 0 through 14 in the above example) for the horizontal scanning signal is transferred to the D/A converter for the horizontal scanning signal, thereby to obtain the analog horizontal scanning signal, with which the deflecting coil 3 for the horizontal scanning can be driven. On the other hand, the coordinate data (bits 0 through 14 in the above example) for the vertical scanning signal is transferred to the D/A converter for the vertical scanning signal, thereby to obtain the analog vertical scanning signal, with which the deflecting coil 3 for the vertical scanning can be driven. It is consequently permitted to change-over the coordinate data in the FIFO memory 113 directly by the value 0 or 1 of the bit 15, to transfer the coordinate data to the D/A converter for the horizontal scanning signal or the D/A converter for the vertical scanning signal at a very high speed, and to generate the respective scanning signals independently of each other. Likewise, it is permitted to generate a signal for the horizontal direction (X-direction) and a signal for the vertical direction (Y-direction) at high speed for each of the astigmatism compensating coil 4, the dynamic focusing coil 5, etc. on the basis of the coordinate data in the FIFO memory 113, and to control the signals at high speed independently of each other. In this manner, the horizontal and vertical signals to be fed to each of the coils can be controlled independently of each other in accordance with the coordinate data in the FIFO memory 113. It is therefore permitted to generate the desired signal in such a way that any coordinate data in the FIFO memory 113 is designated from a display application or the like.

As explained above, one set of scanning signals (horizontal scanning signal and vertical scanning signal) are obtained in the construction of FIGS. 3(a) and 3(b). However, values may well be set in the coordinate data so as to generate the enlarged images of the five points already stated; central point, left upper point, left lower point, right lower point and right upper point. Alternatively, arithmetic circuits may well be disposed on the output sides of the D/A converters shown in FIG. 3(a). In this case, enlargement ratios and shift magnitudes are inputted on the basis of commands from the coordinate data (commands for generating signals which form the enlarged images of the five points; central point, left upper point, left lower point, right lower point and right upper point, thereby to successively obtain the scanning signals of the enlarged images (of, for example, 1,000×1,000 pixels) at the five parts; central part, left upper part, left lower part, right lower part and right upper part, having a high definition (of, for example, 16,000×16,000 pixels). The resulting images are respectively displayed on the screen of one display device (all of the five enlarged images are displayed). Herein, focusing adjustments and astigmatism compensations are made for the respective images and are stored. Besides, the remaining part of the screen is scanned through interpolations. Thus, clear images can be displayed over the entire screen (of 16,000×16,000 pixels).

Next, constructions and steps in the case of data-converting a monochromatic image of high definition into a color image and then displaying and printing the color image will be described in detail with reference to FIG. 4(a) through FIG. 6.

Figure 4C:
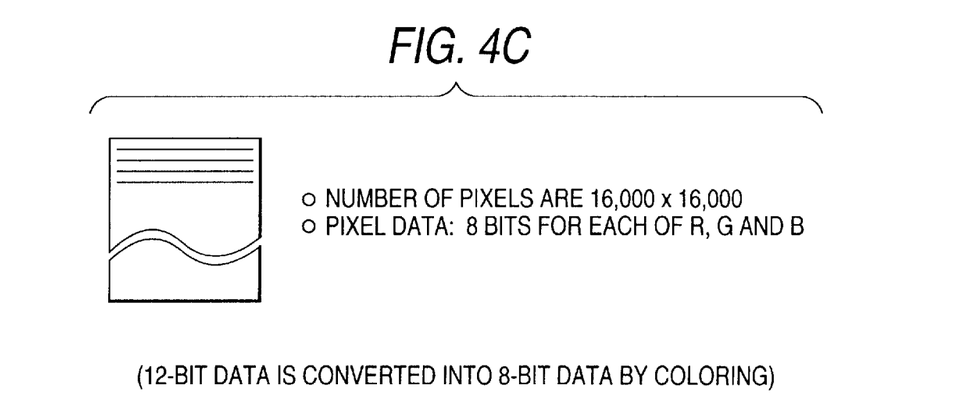

FIGS. 4(a) through 4(c) show diagrams for elucidating data conversion (#1) in the present invention.

FIG. 4(a) shows an example of an adjusting screen (SEM, contrast/brightness). In a state where an SEM image of low resolution is displayed at the left part of the adjusting screen, the contrast and brightness thereof are adjusted. By way of example, an image at the linear scanning of the sample 7 with the electron-beam spot is submitted to amplitude modulation and is displayed as a depicted curve of solid line at the left part of the screen, and a variable resistor for adjusting the brightness and contrast are regulated so that the curve may be confined between depicted reference lines of broken lines. After the adjustments have been completed, the sample 7 is scanned at a high definition so as to load an image of high definition (16,000×16,000 pixels) as shown in FIG. 4(b).

FIG. 4(b) shows an example of the high-definition image. Here, as the high-definition image, the depicted monochromatic image of 16,000×16,000 pixels each being of 12 bits is accepted and is stored in a memory or a hard disk device.

FIG. 4(c) shows an example of the color image. Each pixel of the monochromatic image accepted at the step of FIG. 4(b) has 12 bits. On the other hand, one pixel of the color image is usually expressed by 8 bits of each of colors R, G and B, so that a gradation cannot be expressed by any of the colors R, G and B alone. Therefore, the 12 bits of the monochromatic image pixel are converted into the 8 bits of each of the colors R, G and B by a conversion table of FIG. 6 to be explained later, so as to satisfy the gradation of 12 bits with the colors R, G and B. Thus, each pixel of the monochromatic image can be, in effect, converted into the 8 bits of each of the colors R, G and B while the number of pixels remains unchanged at 16,000×16,000.

Owing to the above, the monochromatic image of high definition is, in effect, converted into the color image without decreasing the number of gradation levels.

Figure 5A:
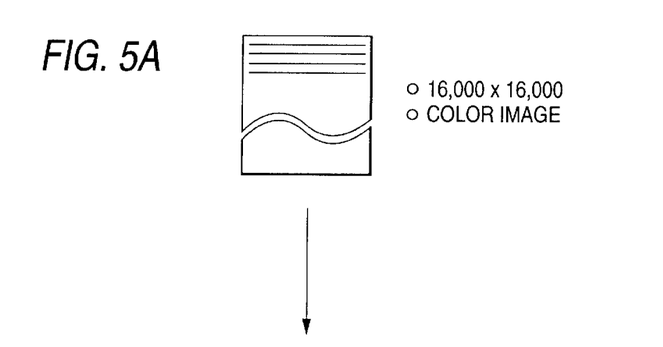
FIGS. 5(a), 5(b) and 5(c) are diagrams for elucidating data conversion (#2) in the present invention.
Figure 5B:
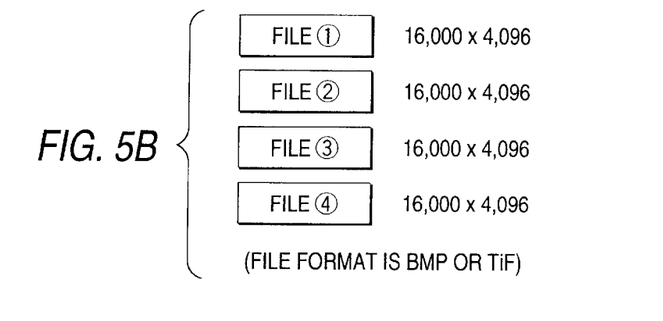
Figure 5C:
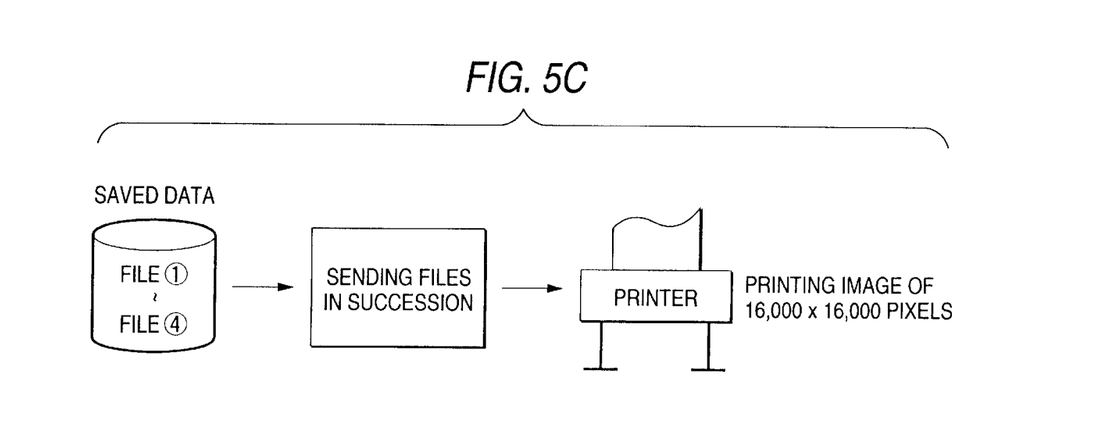

FIGS. 5(a) through 5(c) show diagrams for elucidating data conversion (#2) in the present invention.

FIG. 5(a) shows an example of an image (in colors). Here, the example is the color image obtained through the data conversion as shown in FIG. 4(c) already referred to, and it is expressed by:

16,000×16,000 pixels, and color image (8 bits for each of the colors R, G and B).

FIG. 5(b) shows a situation where the color image depicted in FIG. 5(a) is divided in four here, thereby to create and store files (1), (2), (3) and (4). In the case where the large image is divided into the four files (1), (2), (3) and (4) in this manner, the following effects are brought forth:

When the image is to be referred to or printed out by another application, the reference or the printing is permitted every file.

It is facilitated to transfer and compress a large capacity of high-definition data.

A smaller memory capacity suffices at printing, etc.

FIG. 5(c) shows a printing procedure. Here, since the high-definition color image has been divided in four and saved as the files (1), (2), (3) and (4) at the step of FIG. 5(b), these files are successively fetched and sent to a printer so as to successively print them on a sheet of paper. Thus, the color image composed of 16,000×16,000 pixels can be printed on the sheet of paper.

Figure 6:
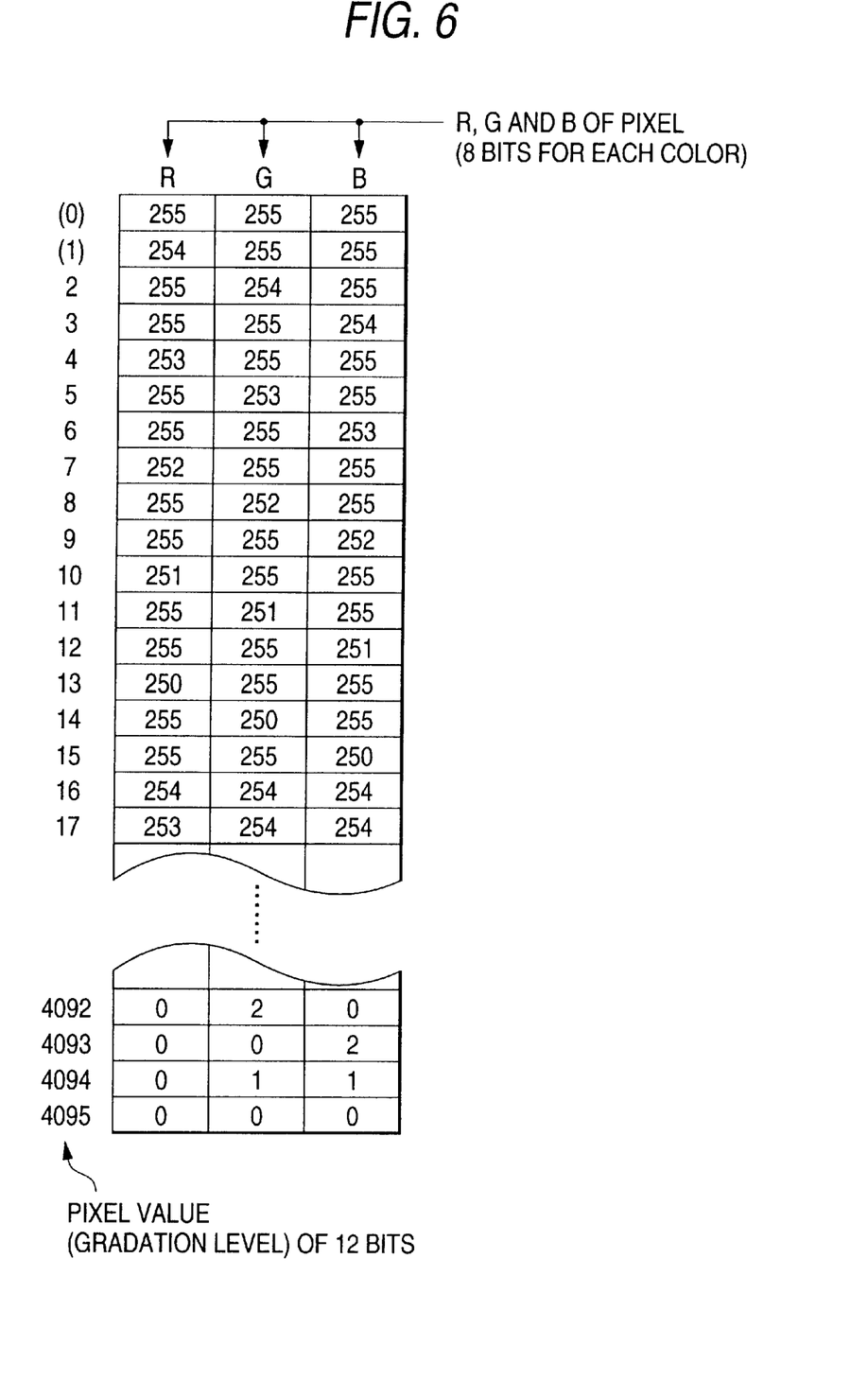
FIG. 6 is a diagram for elucidating an RGB conversion table of 12 bits in the present invention.

FIG. 6 shows a diagram for elucidating the RGB conversion table of 12 bits in the present invention. The RGB conversion table is an example in the case where the pixel value (gradation level) of 12 bits is converted into the gradation levels of 8 bits for each of the signals R, G and B of one pixel. Values found experimentally are set as values resulting from the data conversion into the respective colors R, G and B of 8 bits (–* range of numerical values expressed by 0 through 255) for 0 through 4096 on the left side of the table (a range of numerical values expressed by 12 bits). It is therefore permitted to data-convert the monochromatic image of 12 bits (16,000×16,000 pixels) into the image of 8 bits for each of the colors R, G and B (16,000×16,000 pixels) with the gradation held and at the same number of pixels.

As thus far described, a high-density recording scanning microscope according to the present invention is suited to convert a scanning image at a very high density of, at least, 8,000×8,000 scannings in a scanning microscope, into the digital data of a color image, and to directly print a very clear image of high definition, high gradation and wide view.

What is claimed is:

1. A high-density recording scanning microscope, comprising:

an objective lens which focuses charged particles into a spot and projects the spot on a sample;

scanning means for scanning a surface of the sample with the charged particle spot focused by said objective lens, at a high density of, at least, 8,000 scannings for printing, and scanning the sample surface in a direction substantially orthogonal to a direction of the first-mentioned scanning, at the high density of, at least, 8,000 scannings, or for scanning said sample surface with the number of scannings at a low density for displaying, said number of scannings being smaller than in the high-density printing, and scanning said sample surface in a direction substantially orthogonal to a direction of the low-density scanning, with said number of scannings being smaller than at the low density;

detection means for detecting a signal generated or absorbed when said sample surface is scanned with the charged particles by said scanning means;

conversion means for converting the signal at said high density as detected by said detection means, into a digital signal;

print means for printing on the basis of the digital signal converted by said conversion means; and display means for displaying on the basis of the signal at said low density as detected by said detection means.

2. A high-density recording scanning microscope as defined in claim 1, wherein during the high-density scanning, a size of the spot is made substantially equal to or somewhat smaller than a scanning interval at said high density by said objective lens or a dynamic focusing coil separately disposed.

3. A high-density recording scanning microscope as defined in claim 1, comprising:

means for storing in a memory said digital signal converted by said conversion means;

said print means printing on the basis of said digital signal read out of said memory.

4. A high-density recording scanning microscope as defined in claim 1, wherein the detected signal is converted into a digital color signal.

5. A high-density recording scanning microscope as defined in claim 1, comprising:

a table in which color gradation levels corresponding to gradation levels of the detected signal are registered;

said detected signal is converted into a color signal by reference to said table.

6. A high-density recording scanning microscope as defined in claim 1, wherein in converting the detected signal into a color signal, said detected signal is converted into a gradation level of the color signal corresponding to a gradation level of said detected signal, on the basis of two designated colors.

7. A high-density recording scanning microscope as defined in claim 1, wherein the detected signal is set at, at least, 8 bits, and when a color signal into which said detected signal is converted consists of R, G and B signals, each of them is composed of 8 bits, or when the color signal is for the printing, the color signal has colors in a color data format for use in the printer, and the number of bits of the colors.

* * * * *